(12) United States Patent
Casimir et al.

(10) Patent No.: US 9,611,250 B2
(45) Date of Patent: Apr. 4, 2017

(54) PROCESS FOR PREPARING 4-(CYCLOPROPYLMETHOXY)-N-(3,5-DICHLORO-1-OXIDO-4-PYRIDYL)-5-METHOXYPYRIDINE-2-CARBOXAMIDE

(71) Applicant: SANOFI, Paris (FR)

(72) Inventors: Jean-Paul Casimir, Paris (FR); Guy Rossey, Paris (FR); Christian Wehrey, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/647,760

(22) PCT Filed: Nov. 28, 2013

(86) PCT No.: PCT/EP2013/074970
§ 371 (c)(1),
(2) Date: May 27, 2015

(87) PCT Pub. No.: WO2014/083106
PCT Pub. Date: Jun. 5, 2014

(65) Prior Publication Data
US 2015/0307474 A1    Oct. 29, 2015

(30) Foreign Application Priority Data

Nov. 28, 2012 (FR) ...................... 12 61351

(51) Int. Cl.
| | |
|---|---|
| *C07D 213/62* | (2006.01) |
| *C07D 401/00* | (2006.01) |
| *C07D 211/72* | (2006.01) |
| *C07D 211/84* | (2006.01) |
| *C07D 213/69* | (2006.01) |
| *C07D 213/70* | (2006.01) |
| *C07D 401/12* | (2006.01) |
| *C07D 401/06* | (2006.01) |

(52) U.S. Cl.
CPC ......... *C07D 401/12* (2013.01); *C07D 213/69* (2013.01); *C07D 401/06* (2013.01)

(58) Field of Classification Search
None
See application file for complete search history.

(56) References Cited

FOREIGN PATENT DOCUMENTS

| | | | |
|---|---|---|---|
| EP | 0882714 A | * | 9/1998 |
| EP | 0 882 714 A1 | | 12/1998 |
| WO | WO 95/04045 A1 | * | 2/1995 |
| WO | WO-95/04045 A1 | | 2/1995 |

OTHER PUBLICATIONS

Agami, C. et al. The reactivity of the N-Boc protecting group: an underrated feature. Tetrahedron. 2002, vol. 58, p. 2701.*
International Search Report mailed on Jan. 27, 2014, for PCT Patent Application No. PCT/EP2013/074970, filed on Nov. 28, 2013, four pages.

\* cited by examiner

*Primary Examiner* — Noble Jarrell
*Assistant Examiner* — Ben S Michelson
(74) *Attorney, Agent, or Firm* — Morrison & Foerster LLP

(57) ABSTRACT

The present invention relates to a novel process for preparing the compound 4-(cyclopropylmethoxy)-N-(3,5-dichloro-1-oxido-4-pyridyl)-5-methoxypyridine-2-carboxamide of formula (1), in base or hydrate form or in the form of pharmaceutically acceptable salts, and also to several novel synthetic intermediates that are useful in this preparation process.

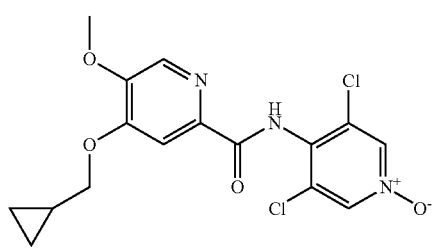

10 Claims, No Drawings

PROCESS FOR PREPARING 4-(CYCLOPROPYLMETHOXY)-N-(3,5-DICHLORO-1-OXIDO-4-PYRIDYL)-5-METHOXYPYRIDINE-2-CARBOXAMIDE

CROSS-REFERENCE TO RELATED APPLICATIONS

This application is a National Phase application under 35 U.S.C. §371 of International Application No. PCT/EP2013/074970 filed Nov. 28, 2013, and claims the benefit of priority of French Application No. 1261351 filed Nov. 28, 2012, the disclosures of each of which are incorporated herein by reference in their entirety.

The present invention relates to a novel process for preparing the compound 4-(cyclopropylmethoxy)-N-(3,5-dichloro-1-oxido-4-pyridyl)-5-methoxypyridine-2-carboxamide, and also to several novel synthetic intermediates that are useful in this preparation process.

The compound 4-(cyclopropylmethoxy)-N-(3,5-dichloro-1-oxido-4-pyridyl)-5-methoxypyridine-2-carboxamide and preparation processes are described in document WO 95/04045. The subject of the present invention is a novel, robust synthetic process, which may be adapted to the industrial scale, for producing the desired compound in large amounts and for obtaining this compound in sufficiently pure form, i.e. without the formation of undesirable byproducts.

The present invention relates to a novel process for preparing the compound 4-(cyclopropylmethoxy)-N-(3,5-dichloro-1-oxido-4-pyridyl)-5-methoxypyridine-2-carboxamide (compound 1) corresponding to the following formula:

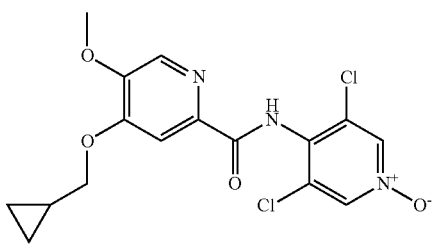

in base or hydrate form, or in the form of pharmaceutically acceptable salts.

Document WO 95/04045 describes several general access routes for obtaining a set of compounds corresponding to the general formula (I), which may, according to a particular combination of substituents, define a compound of formula 1.

According to a first approach described in WO 95/04045, in the scheme below, a compound of general formula (I) may be obtained by reacting the compound of formula (II) with a compound of formula (III).

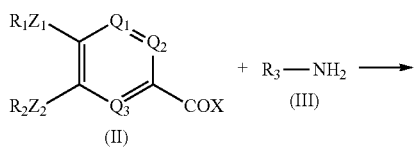

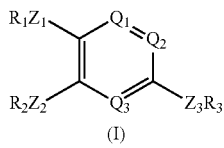

In this scheme, R1, R2, R3, Q1, Q2, Q3, Z1 and Z2 are as described in WO 95/04045. X represents a halogen atom. The reaction takes place in the presence of a base such as an alkali metal hydride, such as sodium hydride, or an amine, preferably a tertiary amine, such as triethylamine or pyridine, optionally in an inert solvent such as dichloromethane or dimethylformamide, or an ether, such as diethyl ether or tetrahydrofuran.

Alternatively, a compound of general formula (I) may be obtained by reacting the compound of formula (II) with a compound of the following formula (IV) $R_4CONHR_3$, in which R4 represents an alkyl or a cycloalkyl group containing up to 5 carbon atoms.

The compound of general formula (II) may be obtained from a compound of formula (XIX) below:

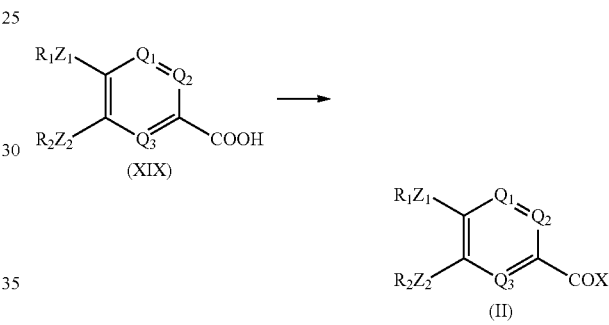

The compound of general formula (XIX) may be obtained from a compound of formula (XVIII) below:

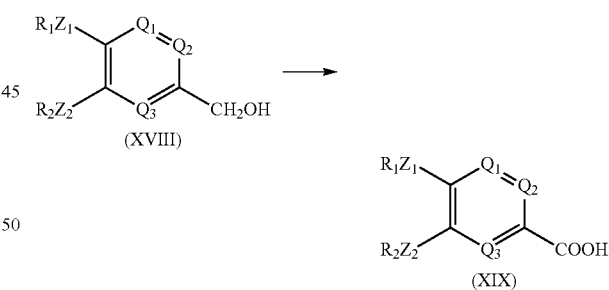

The operating conditions for the synthesis of compounds of formula (I) as they are described in document WO 95/04045 are restricting and cannot be transposed to an industrial scale for safety reasons, and, furthermore, they are accompanied by the formation of a trichloro impurity of compound 1, which is difficult to remove.

The compound of formula 1 may also be obtained according to an 11-step process illustrated by scheme 1. According to this process, the final compound is obtained via a stage of alkylation of the dihydropyridinone ester (5) with bromomethylcyclopropane, followed, after saponification, by amidation with monoacetylated 3,5-dichloroaminopyridine N-oxide.

Scheme 1

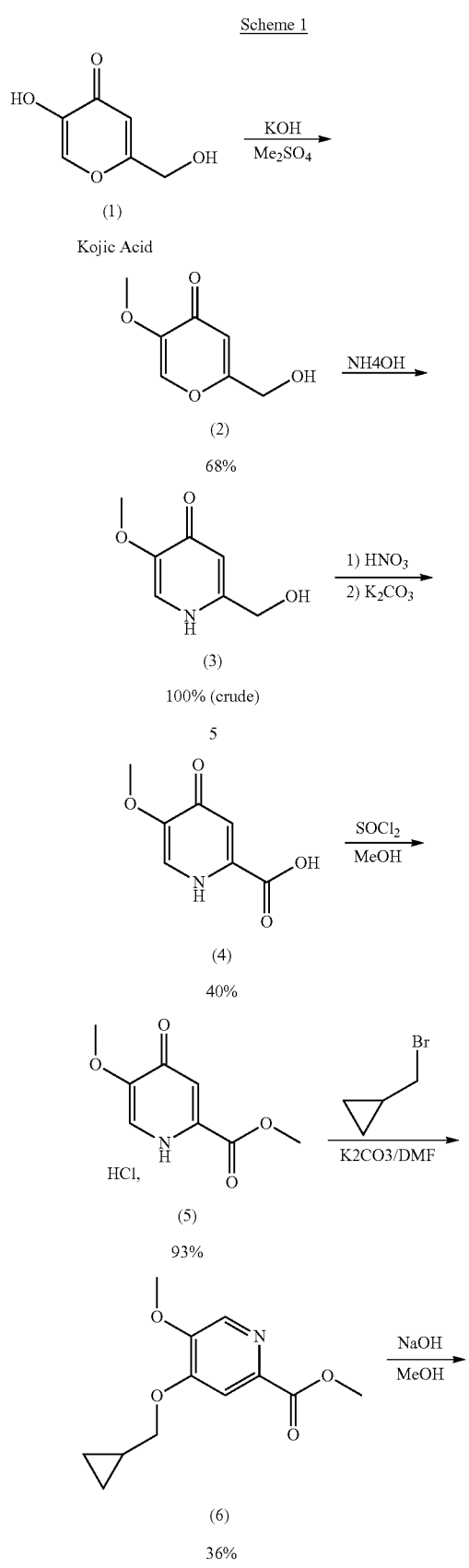

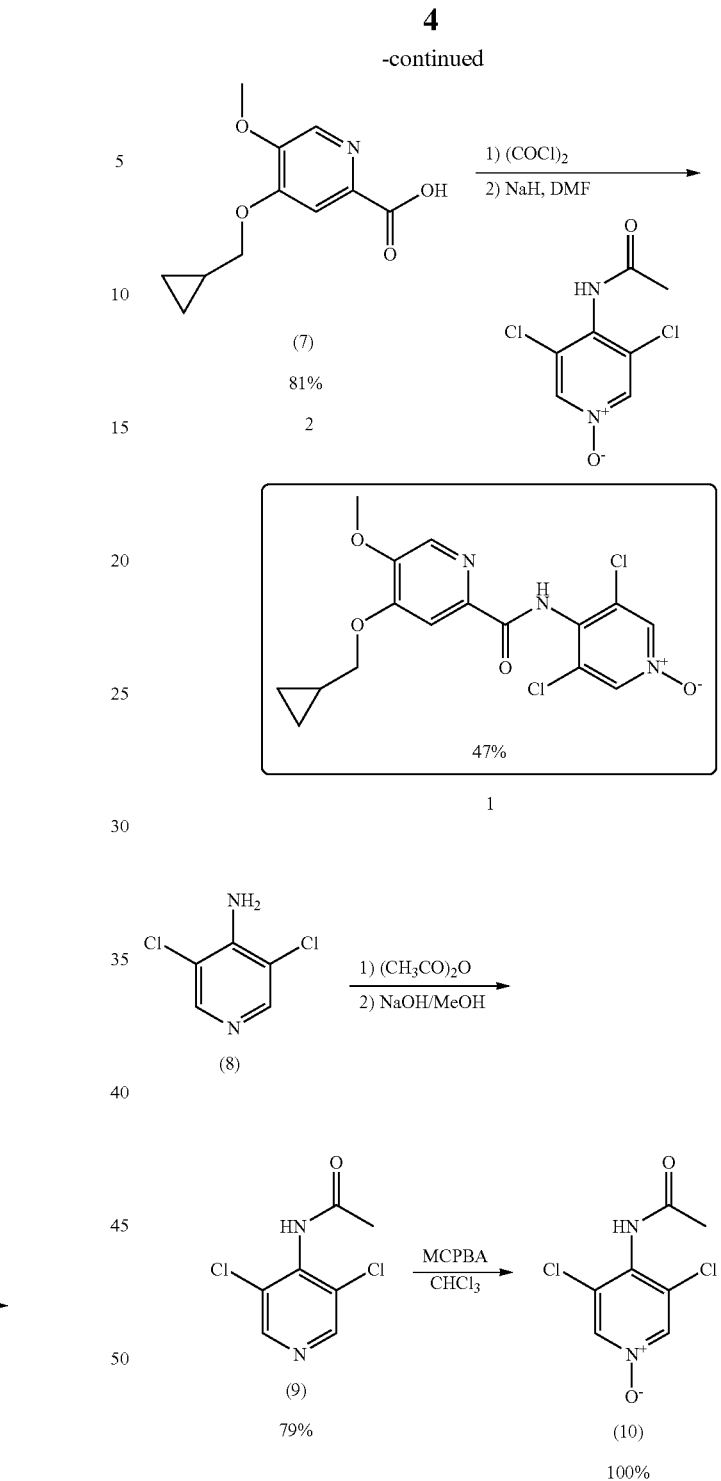

The various aspects of the present invention make it possible to optimize the process for manufacturing the compound of formula 1 by reducing the number of steps, making the process industrializable at a large scale and reducing the amount of impurities.

According to the present invention, the process for synthesizing the compound of formula 1 comprises steps a) to c) represented in scheme 2 below.

Scheme 2

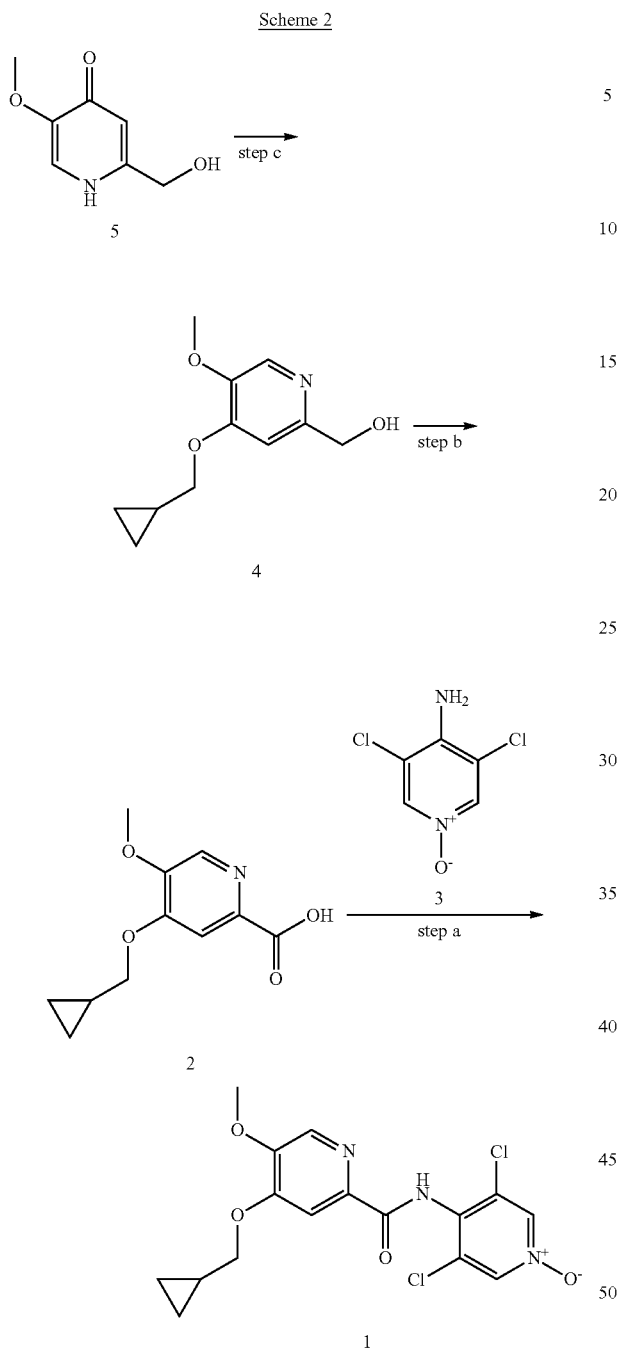

Scheme 3

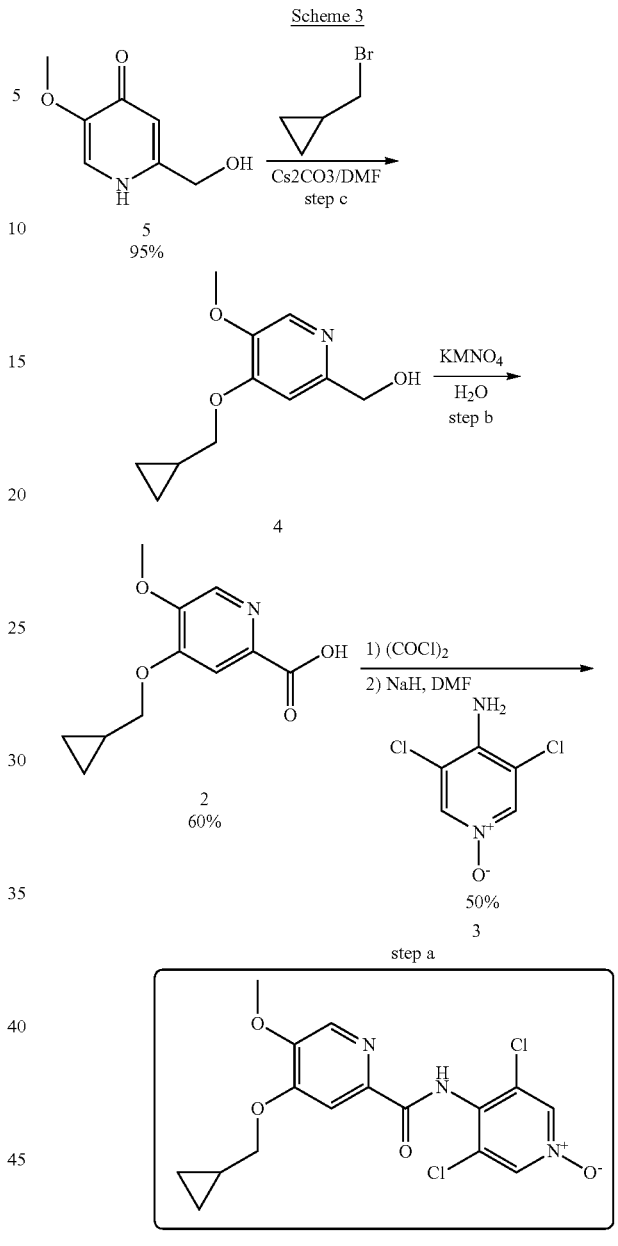

According to a first aspect of the present invention, the synthesis of the compound of formula 1 was simplified by performing a direct O-alkylation of compound 5 (2-hydroxymethyl-5-methoxy-4-pyrid-(1H)-one) with a methylcyclopropane derivative, more particularly with methylcyclopropane bromide (scheme 3). This makes it possible to avoid the sequence of methylation and demethylation of the carboxylate (scheme 1) and thus to reduce the number of steps leading to compound 2 (4-cyclopropylmethoxy-5-methoxypyridine-2-carboxylic acid).

The synthesis according to scheme 3 also poses the problem of the selectivity between N-alkylation and O-alkylation of this type of dihydropyrimidinone analogue 5. The inventors have shown that, as a function of the operating conditions, it was possible to orient the reaction towards the very predominant formation of the O-alkylation product 4. Specifically, the inventors have demonstrated that high-temperature heating, for example at 80° C., of the mixture as defined in step c) of scheme 3, makes it possible to obtain more than 60% of O-alkylation product. The inventors have also shown that this yield is increased when the methylcyclopropane bromide is introduced hot into the reaction mixture preheated to high temperature, for example to 80° C. In the latter process, the "enolate/amide" equilibrium is manifestly shifted towards formation of the alkoxide, leading almost exclusively to the O-alkylation product 4.

This novel synthetic route (scheme 3) thus makes it possible to obtain the compound of formula 1 by reducing the number of stages from 11 to 7 and with an overall yield of 15% instead of 3.5% (scheme 1).

Another advantage of the process according to the present invention is that the gain in selectivity of the stage for O-alkylation of the dihydropyridinone intermediate (compound 5) leads to a relatively pure product which does not require purification by chromatography.

These results make the synthesis compatible with possible operating unit (OU) assemblies.

According to this first aspect, the present invention also relates to compound 4, CH₂OH intermediate, 4-cyclopropylmethoxy-5-methoxy-2-hydroxymethylpyridine, which is useful as an intermediate product.

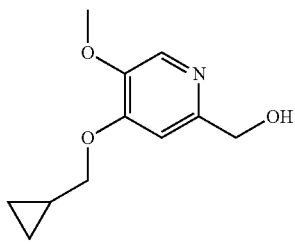

4

According to a second aspect of the present invention, the inventors have also optimized step b) of the process (scheme 4), leading from compound 4 to compound 2 via a "one-pot" process according to the reaction below.

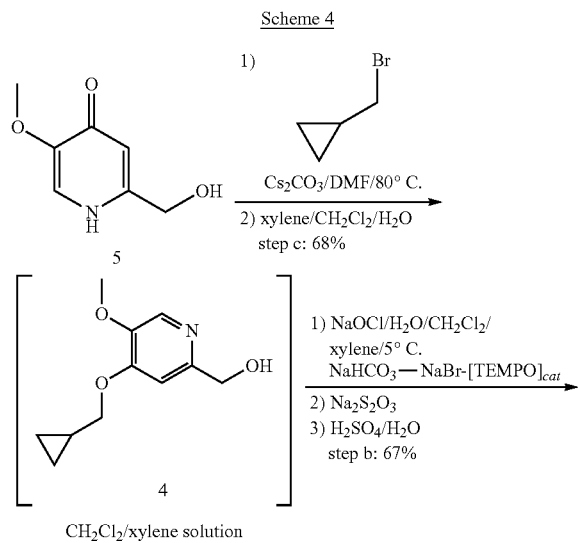

According to a third aspect of the present invention, novel alternative processes that are compatible with industrialization were developed on step a).

A first process involves an amidation reaction with the cyclic trimer of n-propylphosphonic anhydride (T3P) between the acid and the N-oxide (scheme 5):

Scheme 5

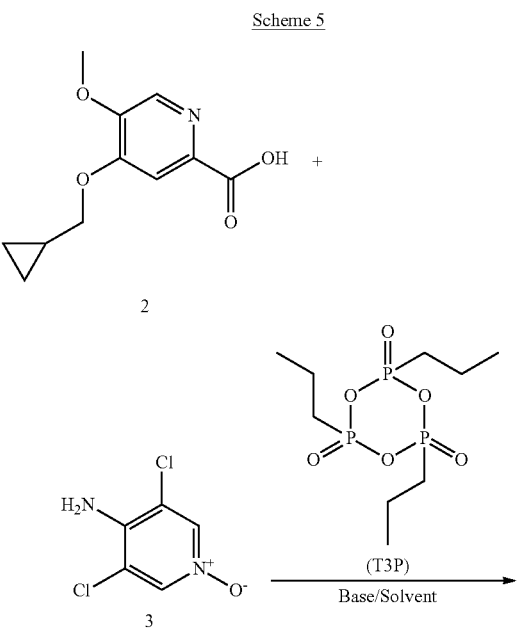

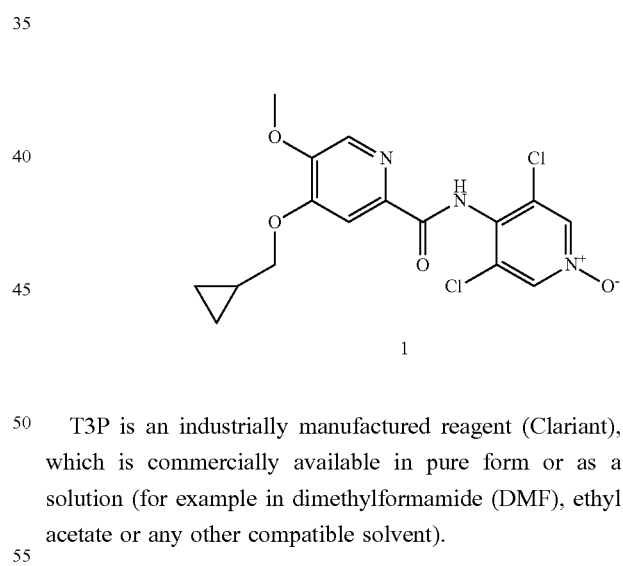

1

T3P is an industrially manufactured reagent (Clariant), which is commercially available in pure form or as a solution (for example in dimethylformamide (DMF), ethyl acetate or any other compatible solvent).

Furthermore, in the presence of 4-dimethylaminopyridine (DMAP/minimum of 0.2 equivalent), at about 75° C., all of the diacyl is converted into final product which is isolated by simple precipitation in aqueous medium and recrystallization from isopropanol, with a yield of about 80% and in microanalytical grade (scheme 6).

Use of the reagent T3P and of catalysis with DMAP affords a quality sufficient for the manufacture of batches intended for human use.

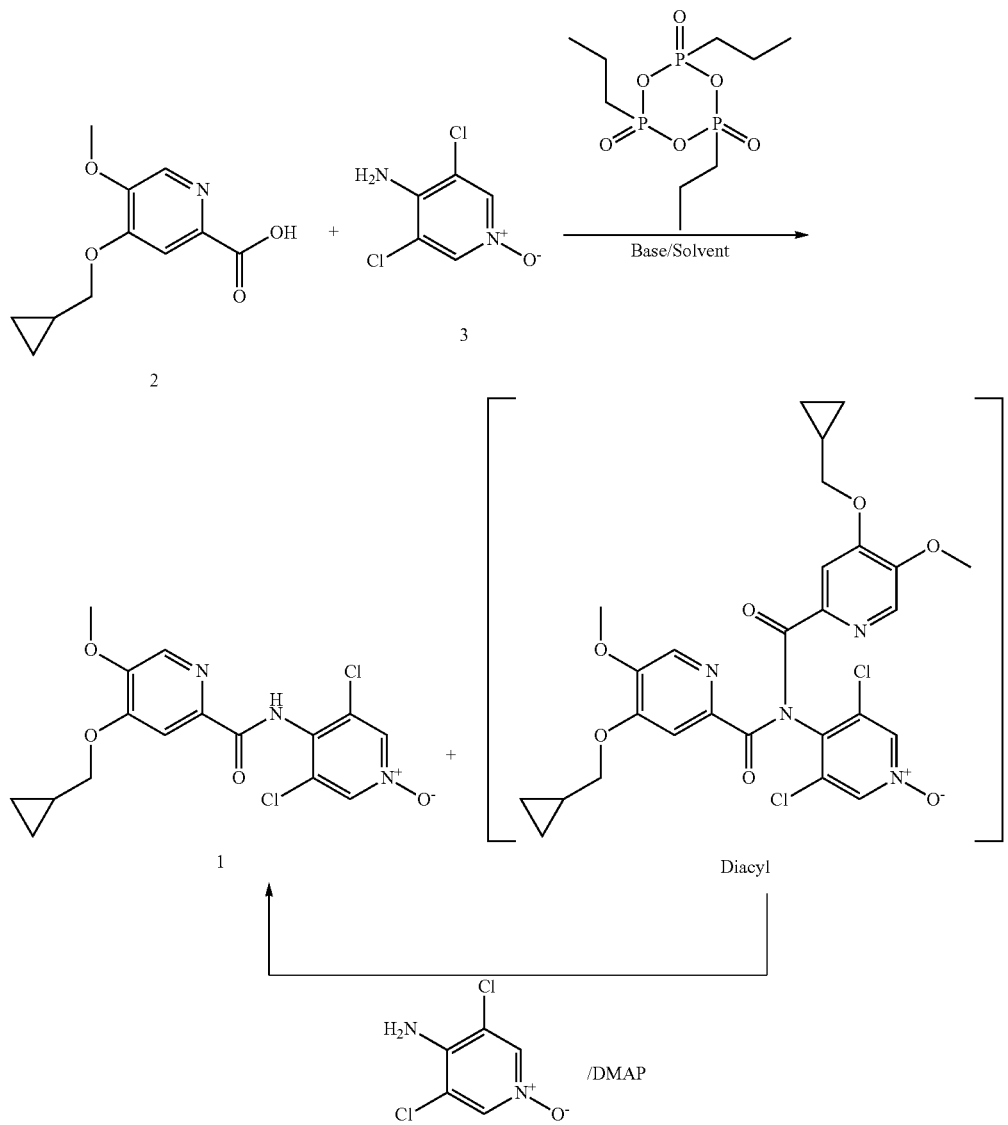
Alternatively, a second process involves a coupling reaction between the acid imidazolide and the N-oxide (scheme 7).
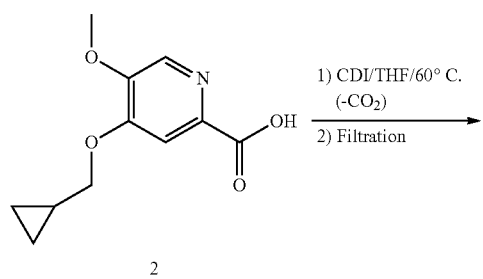

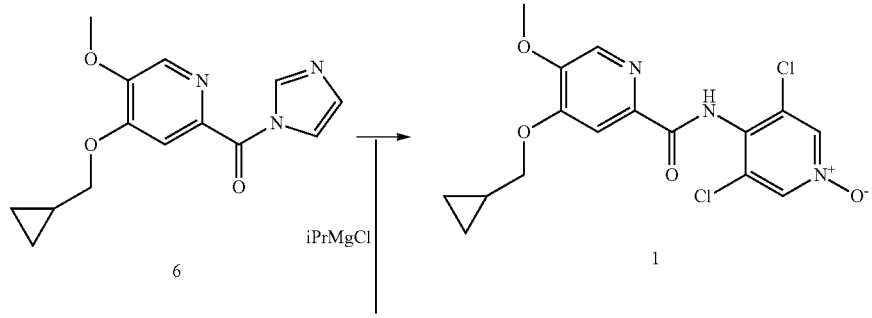

This very convenient activation method makes it possible to avoid the use of corrosive reagents such as thionyl chloride and to work under less drastic water exclusion conditions, since the imidazolide is less sensitive to water than the corresponding acid chloride.

The imidazolide is prepared by heating the acid in the presence of carbonyldiimidazole (CDI) in tetrahydrofuran (THF) or methyl-THF, and is isolated by cold filtration. The imidazole formed remains soluble and is thus removed. The anion of the N-oxide is obtained by deprotonation using an organomagnesium reagent. Cyclohexylmagnesium chloride (CyMgCl) or isopropylmagnesium chloride (iPrMgCl) is suitable for use, and these reagents are available cheaply, on an industrial scale. For safety reasons, CyMgCl is preferable to iPrMgCl, which, during the deprotonation of the N-oxide, leads to the formation of propane, a flammable gas.

The coupling with the imidazolide is performed by refluxing in THF (4 to 5 hours). The expected product is extracted after aqueous hydrolysis (aqueous NH$_4$Cl) which is preferable to phosphates on account of the risk of coprecipitation of magnesium phosphates) and purified by recrystallization (iPrOH or n-PrOH).

Another subject of the present invention relates to the imidazolide intermediate of formula 6 having the following formula:

Alternatively, a third process involves amidation with carbodiimide of the compound of formula 2 and the N-Boc derivative of compound 3 (N-Boc-dichloropyridoxide). The compound of formula 1 is obtained by hydrolysis of the Boc group in acidic medium (scheme 8).

Scheme 8:

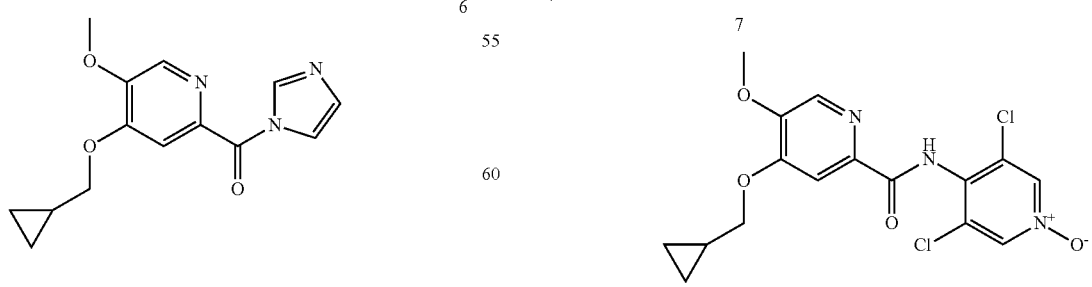

The precursor N-Boc-dichloropyridoxide may be synthesized according to the following two methods (scheme 9):

1) from dichloropyridoxide via treatment with Boc$_2$O (2 equivalents/room temperature/3 hours) followed by a mono-deprotection via methanolysis: this method is preferred to method 2) since the dichloropyridoxide is much more reactive than aminodichloropyridine towards Boc$_2$O.

2) from 4-amino-3,5-dichloropyridine, by treatment with Boc$_2$O (4 equivalents/refluxing THF/30 hours), mono-deprotection via methanolysis and then N-oxidation with meta-chloroperbenzoic acid.

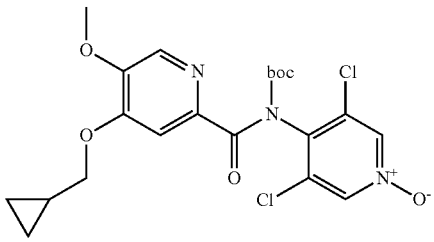

According to the invention, the process for synthesizing the compound of formula 1 comprises steps a) to c) represented in scheme 2 below.

Scheme 9

Method 1):

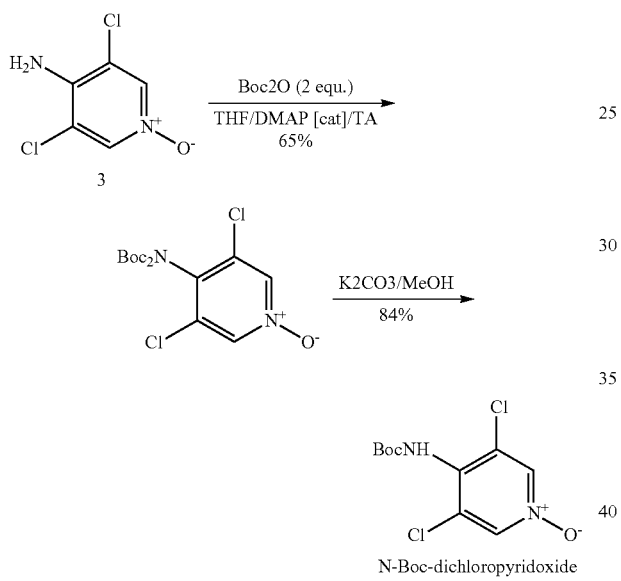

Method 2):

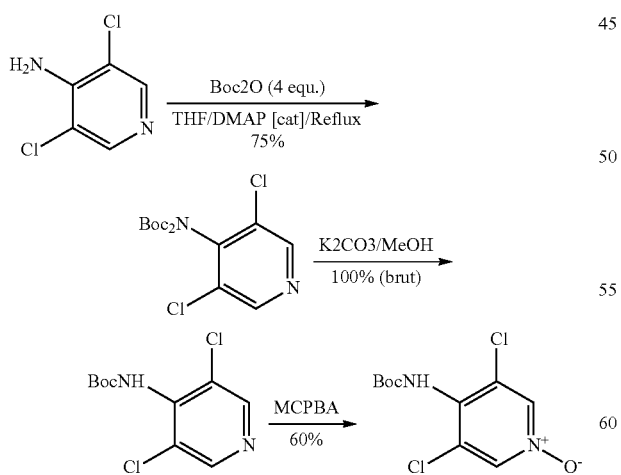

Scheme 2

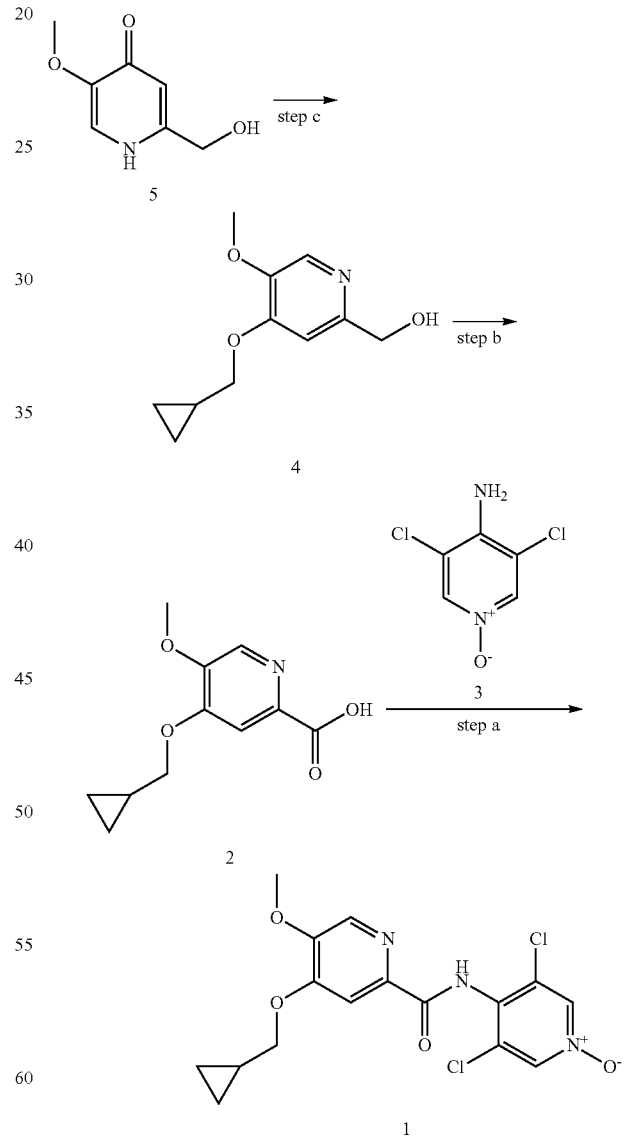

Another subject of the present invention relates to the intermediate of formula 7, an N-Boc derivative of compound 1, having the following formula:

According to the invention, the process for synthesizing the compound of formula 1 is characterized in that it comprises the following steps:

step a) coupling reaction, optionally in the presence of catalysis with DMPA
    with the cyclic trimer of n-propylphosphonic anhydride T3P; or
    with carbonyldiimidazole (CD) with compound 3 or the N-Boc derivative thereof.
step b): "one-pot" oxidation reaction
step c) of O-alkylation: reaction of the compound 2-hydroxymethyl-5-methoxy-4-pyrid-(1H)-one of formula 5 with a methylcyclopropane derivative, such as methylcyclopropane bromide, and a base, such as caesium carbonate, in a polar aprotic solvent such as DMF (dimethylformamide).

Alternatively, steps b) and c) may be performed without isolating compound 4.

DEFINITIONS

The term "base" means organomagnesium reagents such as cyclohexylmagnesium chloride, isopropylmagnesium chloride or benzylmagnesium chloride; hexyllithium; hydrides; or caesium carbonate.

The term "polar aprotic solvent" means ethers such as THF (tetrahydrofuran), MeTHF (methyltetrahydrofuran), DME (dimethoxyethane), MTBE (methyl tert-butyl ether) or dioxane, chlorinated solvents such as dichloromethane, 1,2-dichloroethane, nitriles such as acetonitrile, ketones such as acetone, methyl ethyl ketone or methyl isobutyl ketone, amides such as DMF (dimethylformamide), DMAC (dimethylacetamide) or NMP (N-methylpyrrolidone).

The term "apolar aprotic solvent" means aromatic solvents such as toluene, xylene or chlorobenzene, and esters such as ethyl acetate or butyl acetate.

The term "polar protic solvent" means alcohols such as methanol, ethanol, isopropanol or butanol.

The term "strong acid" means hydrochloric acid, sulfuric acid, sulfonic acid, methanesulfonic acid, para-toluenesulfonic acid, phosphoric acid or acetic acid.

Another subject of the present invention relates to the process for preparing the compound of formula 1, characterized in that it comprises at least one of the steps a), b) or c) as described above and below, or characterized in that it comprises all the steps a) to c).

Another subject of the present invention relates to a novel process for preparing the compound of formula 1, characterized in that step c) is a direct O-alkylation.

More particularly, another subject of the present invention relates to the process for synthesizing the compound of formula 1, comprising step c) or comprising steps a) to c), characterized in that the alkylating agent is methylcyclopropane bromide. More particularly, another subject of the present invention relates to the process for synthesizing the compound of formula 1, comprising step c) or comprising steps a) to c), characterized in that the base is caesium carbonate. More particularly, another subject of the present invention relates to the process for synthesizing the compound of formula 1, comprising step c) or comprising steps a) to c), characterized in that the polar aprotic solvent is dimethylformamide.

More particularly, another subject of the present invention relates to the process for synthesizing the compound of formula 1, comprising step c) or comprising steps a) to c), characterized in that the O-alkylation reaction takes place at a temperature of at least 80° C.

More particularly, another subject of the present invention relates to the process for synthesizing the compound of formula 1, comprising step c) or comprising steps a) to c), characterized in that the dimethylformamide and the caesium carbonate are preheated to a temperature of at least 80° C. and the methylcyclopropane bromide is introduced hot.

Another subject of the present invention relates to a novel process for preparing the compound of formula 1, characterized in that step b) is a "one-pot" step.

Another subject of the present invention relates to a novel process for preparing the compound of formula 1, characterized in that step a) is a step of amidation with the cyclic trimer of n-propylphosphonic anhydride (T3P). More particularly, this step is performed in the presence of 4-dimethylaminopyridine.

Another subject of the present invention relates to a novel process for preparing the compound of formula 1, characterized in that step a) is a step of coupling between the imidazolide of compound 2 (4-cyclopropylmethoxy-5-methoxy-2-pyridinecarboxylic acid imidazolide) and monoacetylated 3,5-dichloroaminopyridine N-oxide. More particularly, this step is performed in the presence of cyclopropylmagnesium chloride.

Another subject of the present invention relates to a novel process for preparing the compound of formula 1, characterized in that step a) is a step of carborimide-mediated amidation between compound 2 (4-cyclopropylmethoxy-5-methoxy-2-pyridinecarboxylic acid) and the N-Boc derivative of compound 3 (3,5-dichloroaminopyridine N-oxide). More particularly, this step is performed in the presence of 4-dimethylaminopyridine.

Another subject of the present invention relates to the compound of formula 4.

Another subject of the present invention relates to the compound of formula 6.

Another subject of the present invention relates to the compound of formula 7.

Another subject of the present invention relates to the use of one or more of the compounds of formulae 4, 6 and 7 as intermediate compound in the process for preparing the compound of formula 1.

According to one of the aspects of the present invention, it was especially possible to identify the following impurities:

Compound I.1: 4-(cyclobutyloxy)-N-(3,5-dichloro-1-oxido-4-pyridyl)-5-methoxypyridine-2-carboxamide Molecular formula: C16H15Cl2N3O4, Relative molecular mass: 384.22

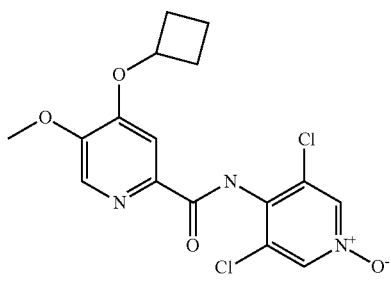 [SMILES: COc1cnc(C(=O)Nc2c(Cl)c[n+]([O-])cc2Cl)cc1OC1CCC1]

Compound I.2: 4-Cyclopropylmethoxy-5-methoxy-pyridine-2-carboxylic acid (4-cyclopropylmethoxy-5-methoxypyridine-2-carbonyl)-(3,5-dichloro-1-oxy-4-pyridyl)amide Molecular formula: C27H26Cl2N4O7, Relative molecular mass: 589.44

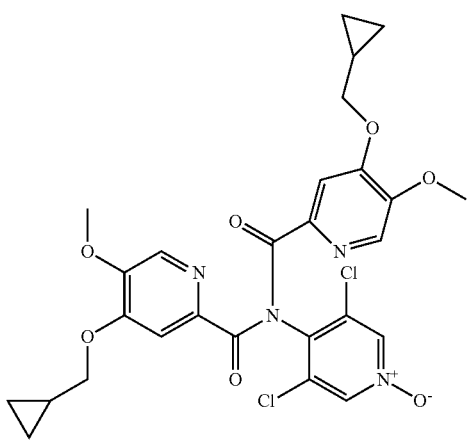 [SMILES: COc1cnc(C(=O)N(C(=O)c2cc(OCC3CC3)c(OC)cn2)c2c(Cl)c[n+]([O-])cc2Cl)cc1OCC1CC1]

Compound I.3: 4-(cyclopropylmethoxy)-N-(3,5-dichloro-4-pyridyl)-5-methoxypyridine-2-carboxamide Molecular formula: C16H15Cl2N3O3, Relative molecular mass: 368.22

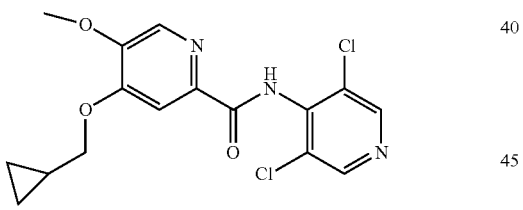

The identification of one or more of these compounds may be useful as a marker of the process for preparing the compound of formula 1 according to the present invention.

Detailed examples of preparation according to the claimed processes are described below. These examples are not limiting and merely illustrate the present invention.

EXAMPLE 1 synthesis of the CH₂OH intermediate (4-cyclopropylmethoxy-5-methoxy-2-hydroxymethylpyridine, compound 4) by direct O-alkylation By heating at 80° C. (15 minutes) a mixture of 2-hydroxymethyl-5-methoxy-4-pyrid-(1H)-one (compound 5), caesium carbonate (1.5 equivalents) and bromomethylcyclopropane (1 equivalent) in 10 volumes of DMF, a mixture is formed, of the N-alkylation product (30% to 40%) and of the O-alkylation product (60% to 70%):

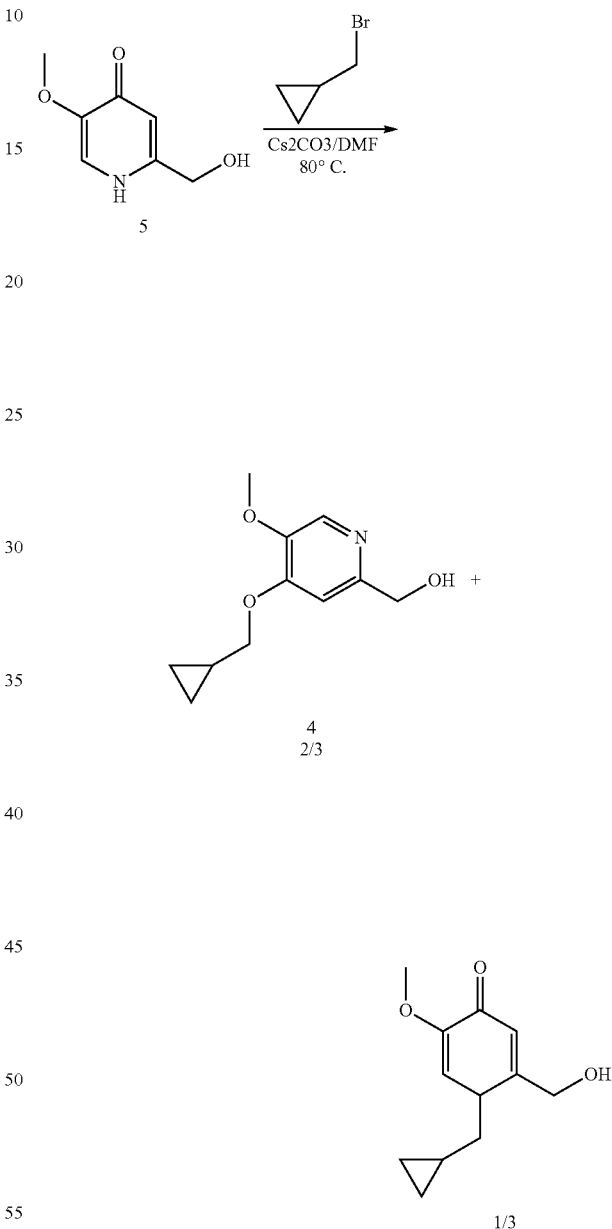

On the other hand, if compound 5 is preheated to 80° C. in DMF in the presence of Cs₂CO₃, the methylcyclopropane bromide being introduced hot, the expected O-alkylation product is formed almost exclusively, the enolate/amide equilibrium being manifestly shifted under these conditions towards the formation of the alkoxide:

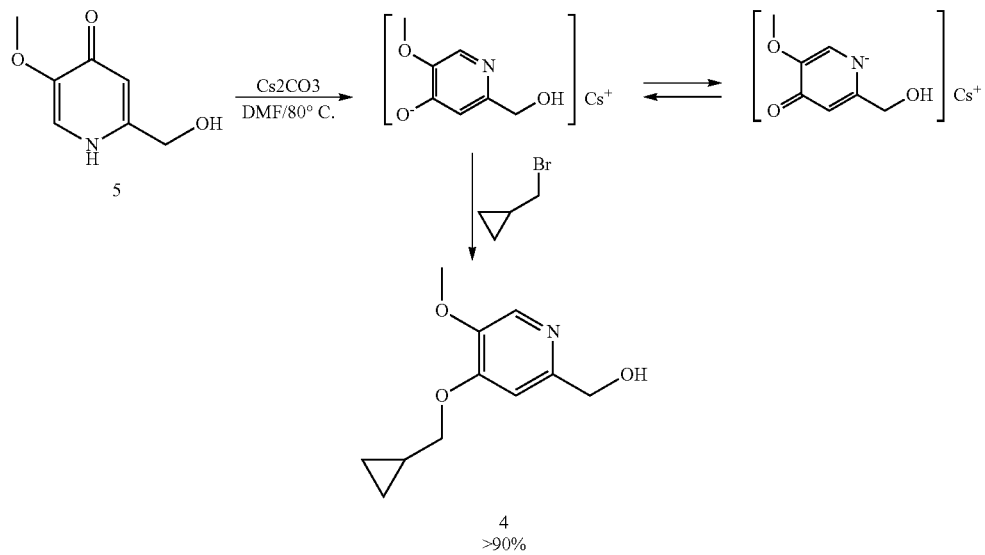

The possible traces of N-alkylation product that may appear are removed during the treatment by washing with water, which makes this process compatible with OU assemblies. The yield of compound 4 is greater than or equal to 75%.

EXAMPLE 2 synthesis of 4-cyclopropylmethoxy-5-methoxypyridine-2-carboxylic acid

A suspension containing methoxypyridone monohydrate (OU) in 7 volumes of DMF is concentrated and dried down to 2 volumes by distillation under vacuum with DMF. After adding caesium carbonate (1.1 equivalents/dry), this suspension is preheated to about 85° C. At this temperature, bromomethylcyclopropane is added over about 30 minutes (1.05 equivalents/dry—exothermic reaction). After cooling to room temperature, the mineral salts are removed by filtration and the DMF is distilled off by azeotropic entrainment with xylene. The concentrate is taken up in methylene chloride and washed with water. The chloromethylene extraction phase containing the expected product 4 (8 volumes at about 0.5 M/yield of about 80%) is used as obtained for the following stage.

To a two-phase system of methylene chloride (about 8 volumes at about 15 m/m % of xylene)/water (20 volumes) containing cyclopropylpyridinol (OU), sodium bicarbonate (1.0 equivalent), sodium bromide (0.5 equivalent) and 4-acetamido-TEMPO (0.04 equivalent) is added over about 1 hour at 0-5° C., with vigorous stirring, an aqueous bleach solution at about 2M (2.4 equivalents/5.9 volumes). After stirring for 3 hours at 0-5° C., the excess oxidizing agent is neutralized with aqueous 2M sodium thiosulfate solution (qs, i.e. 0.6 volume in the case described). After cooling to room temperature and separation of the phases by settling, the aqueous phase is concentrated (12 volumes) at standard pressure and the sodium carboxylate precipitate is filtered off and then redissolved in water (about 8 volumes) at 40° C. After acidification to a pH of about 4-5 with sulfuric acid, compound 2 is isolated after crystallization from water at 40° C., in a yield of about 69%.

$^1$H NMR spectrum (400 MHz, δ in ppm, DMSO-d6): 0.36 (m, 2H); 0.59 (m, 2H); 1.24 (m, 1H); 3.95 (s, 3H); 3.97 (d, J=6.8 Hz, 2H); 7.57 (s, 1H); 8.25 (s, 1H)

EXAMPLE 3 synthesis of 4-(cyclopropylmethoxy)-N-(3,5-dichloro-1-oxido-4-pyridyl)-5-methoxypyridine-2-carboxamide To a suspension of the acid of compound 2 (4-cyclopropylmethoxy-5-methoxypyridine-2-carboxylic acid) and of the N-oxide of compound 3 (3,5-dichloro-4-aminopyridine 1-oxide, 1.25 equivalents) in ethyl acetate (EtOAc) (about 10 volumes) is added a solution of T3P at 50% in EtOAc (1.2 equivalents), triethylamine (2.5 equivalents) and DMAP (0.2 equivalent). The mixture is refluxed for about ten hours, allowed to cool, hydrolysed with water, filtered and then washed with water and with EtOAc. The crude compound 1 is isolated in a yield of about 80% and a microanalytical purity of greater than 99%.

$^1$H NMR spectrum (500 MHz, δ in ppm, DMSO-d6): 0.37 (m, 2H); 0.60 (m, 2H); 1.25 (m, 1H); 3.99 (s, 3H); 4.01 (d, J=7.1 Hz, 2H); 7.62 (s, 1H); 8.29 (s, 1H); 8.71 (s, 2H); 10.51 (broad s, 1H)

EXAMPLE 4 synthesis of 4-(cyclopropylmethoxy)-N-(3,5-dichloro-1-oxido-4-pyridyl)-5-methoxypyridine-2-carboxamide A solution of carbonyldiimidazole (CDI, 1.1 equivalents) in methyl-THF (7 volumes) is poured into a suspension of cyclopropylpyridine acid (OU=50 g) in methyl-THF (7 volumes), and heated to 60° C. The evolution of $CO_2$ is controlled by the rate of introduction of the CDI. After heating for 1 to 2 hours at 60° C., the reaction medium is cooled to about 5° C. The imidazolide precipitate is filtered off under nitrogen, washed with a minimum amount of methyl-THF (2 volumes) and dried in a vacuum oven. The imidazolide is isolated in a yield of about 80% and a purity of greater than 95%.

¹H NMR spectrum (400 MHz, δ in ppm, DMSO-d6): 0.39 (m, 2H); 0.62 (m, 2H); 1.28 (m, 1H); 4.01 (s, 3H); 4.04 (d, J=7.0 Hz, 2H); 7.12 (broad s, 1H); 7.73 (s, 1H); 7.95 (broad s, 1H); 8.40 (s, 1H); 8.76 (broad s, 1H)

A suspension of dichloropyridoxide (1.5 equivalents) in 20 volumes of THF is treated at 20-30° C. with cyclohexylmagnesium chloride as a 1.3 M solution in a THF/toluene mixture (1.2 equivalents). After stirring for 3 hours at room temperature, the imidazolide (OU=20 g) suspended in 5 volumes of THF is poured into the amide thus formed. After 5 hours at 60° C. and then cooling to room temperature, the mixture is hydrolysed with aqueous molar ammonium chloride solution (30 volumes), extracted with ethyl acetate (30 volumes), washed with water (10 volumes) and crystallized from isopropanol (15 volumes), after a solvent exchange; compound 1 is isolated by filtration and drying in a yield of about 70% and a microanalytical purity.

¹H NMR spectrum (500 MHz, δ in ppm, DMSO-d6): 0.37 (m, 2H); 0.60 (m, 2H); 1.25 (m, 1H); 3.99 (s, 3H); 4.01 (d, J=7.1 Hz, 2H); 7.62 (s, 1H); 8.29 (s, 1H); 8.71 (s, 2H); 10.51 (broad s, 1H)

EXAMPLE 5 synthesis of 4-(cyclopropylmethoxy)-N-(3,5-dichloro-1-oxido-4-pyridyl)-5-methoxypyridine-2-carboxamide N-Boc Derivative of Compound 1:

A chloromethylene solution of EDC (1-[3-dimethylaminopropyl]-3-ethylcarbodiimide hydrochloride/1.2 equivalents) is added, at about 10° C., to a chloromethylene solution containing cyclopropylpyridine acid (compound 2/OU), N-Boc-dichloropyridoxide (1 equivalent) and DMAP (4-dimethylaminopyridine/0.1 equivalent). After stirring for 18 hours at 20° C., the reaction medium is washed with water and brought to dryness. The N-Boc product of compound 1 is isolated in pure form in a yield of 70% after recrystallization from isopropanol.

¹H NMR spectrum (400 MHz, δ in ppm, DMSO-d6): 0.36 (m, 2H); 0.59 (m, 2H); 1.24 (broad s, 10H); 3.96 (s, 3H); 4.00 (d, J=7.0 Hz, 2H); 7.43 (s, 1H); 8.30 (s, 1H); 8.80 (s, 2H)

Hydrolysis of the Boc and Production of Compound 1:

A chloromethylene solution of the N-Boc derivative of compound 1 is heated at 30° C. for about 4 hours in the presence of trifluoroacetic acid (13 equivalents). Compound 1 is isolated by precipitation, after treatment of the reaction medium with aqueous sodium bicarbonate, in a yield of greater than 70%.

¹H NMR spectrum (500 MHz, δ in ppm, DMSO-d6): 0.37 (m, 2H); 0.60 (m, 2H); 1.25 (m, 1H); 3.99 (s, 3H); 4.01 (d, J=7.1 Hz, 2H); 7.62 (s, 1H); 8.29 (s, 1H); 8.71 (s, 2H); 10.51 (broad s, 1H)

Production of the N-Boc-dichloropyridoxide

Method 1:

A mixture containing THF (10 volumes), Boc₂O (2.2 equivalents), dichloropyridoxide (OU) and DMAP (0.1 equivalent) is stirred at room temperature for 3 hours. The expected N-Boc-dichloropyridoxide product is isolated in a yield of 65%, after distillation of the THF and recrystallization from ethyl acetate.

¹H NMR spectrum (400 MHz, δ in ppm, DMSO-d6): 1.38 (s, 18H); 8.79 (s, 2H)

Method 2:

A mixture containing the dichloropyridoxide compound (OU), potassium carbonate (3 equivalents) and methanol (10 volumes) is refluxed for 3 hours. After filtration of the mineral salts and distillation of the MeOH, the expected N-Boc-dichloropyridoxide product is isolated by extraction with ethyl acetate and washing until neutral with aqueous HCl. The yield obtained is 84%.

¹H NMR spectrum (400 MHz, δ in ppm, DMSO-d6): 1.47 (s, 9H); 8.66 (s, 2H); 9.28 (broad s, 1H).

The invention claimed is:

1. A process for preparing 4-(cyclopropylmethoxy)-N-(3,5-dichloro-1-oxido-4-pyridyl)-5-methoxypyridine-2-carboxamide, in base or hydrate form or in the form of a pharmaceutically acceptable salt, of formula 1 below:

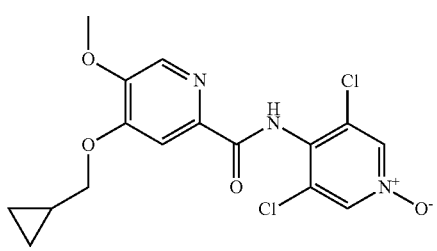

wherein the process comprises:

a step c): reaction of the compound 2-hydroxymethyl-5-methoxy-4-pyrid-(1H)-one of formula 5 with methylcyclopropane bromide and a base, in a polar aprotic solvent, according to the scheme below:

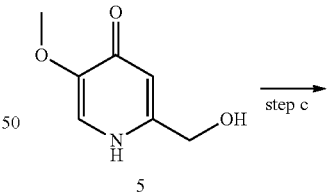

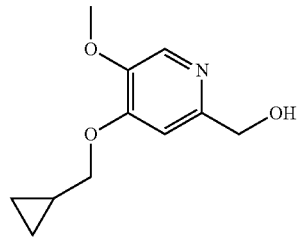

a step b): oxidation reaction of compound 4 obtained in step c), according to the scheme below:

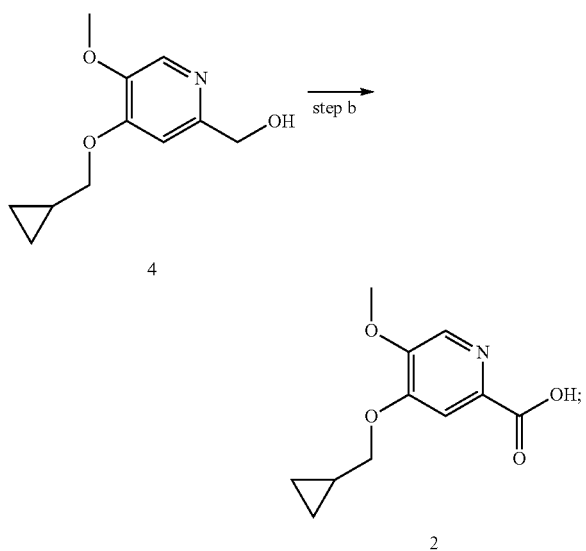

and a step a): coupling reaction of compound 2 obtained in step b) with 3,5-dichloroaminopyridine N-oxide (compound 3) or N-Boc-dichloropyridoxide (compound 3a), according to the scheme below:

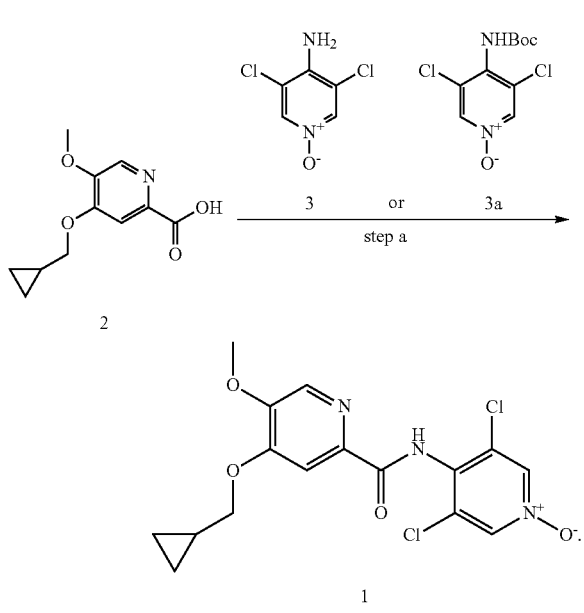

2. The process for preparing 4-(cyclopropylmethoxy)-N-(3,5-dichloro-1-oxido-4-pyridyl)-5-methoxypyridine-2-carboxamide, in base or hydrate form or in the form of a pharmaceutically acceptable salt, according to claim 1, wherein the base is cesium carbonate and the polar aprotic solvent is dimethylformamide.

3. The process for preparing 4-(cyclopropylmethoxy)-N-(3,5-dichloro-1-oxido-4-pyridyl)-5-methoxypyridine-2-carboxamide, in base or hydrate form or in the form of a pharmaceutically acceptable salt, according to claim 1, wherein step b) is a one-pot step.

4. The process for preparing 4-(cyclopropylmethoxy)-N-(3,5-dichloro-1-oxido-4-pyridyl)-5-methoxypyridine-2-carboxamide, in base or hydrate form or in the form of a pharmaceutically acceptable salt, according to claim 1, wherein step a) is an amidation step with the cyclic trimer of n-propylphosphonic anhydride (T3P).

5. The process for preparing 4-(cyclopropylmethoxy)-N-(3,5-dichloro-1-oxido-4-pyridyl)-5-methoxypyridine-2-carboxamide, in base or hydrate form or in the form of a pharmaceutically acceptable salt, according to claim 4, wherein the amidation step is performed in the presence of 4-dimethylaminopyridine.

6. The process for preparing 4-(cyclopropylmethoxy)-N-(3,5-dichloro-1-oxido-4-pyridyl)-5-methoxypyridine-2-carboxamide, in base or hydrate form or in the form of a pharmaceutically acceptable salt, according to claim 1, wherein step a) is a coupling reaction between 4-cyclopropylmethoxy-5-methoxy-2-pyridinecarboxylic acid imidazolide and 3,5-dichloroaminopyridine N-oxide.

7. The process for preparing 4-(cyclopropylmethoxy)-N-(3,5-dichloro-1-oxido-4-pyridyl)-5-methoxypyridine-2-carboxamide, in base or hydrate form or in the form of a pharmaceutically acceptable salt, according to claim 1, wherein step a) is a carbodiimide-mediated amidation between 4-cyclopropylmethoxy-5-methoxy-2-pyridinecarboxylic acid and the N-Boc-dichloropyridoxide.

8. A process for preparing 4-(cyclopropylmethoxy)-N-(3,5-dichloro-1-oxido-4-pyridyl)-5-methoxypyridine-2-carboxamide, in base or hydrate form or in the form of a pharmaceutically acceptable salt, of formula 1 below:

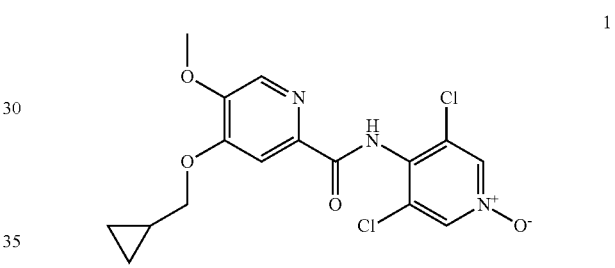

wherein the process comprises a coupling reaction of 4-cyclopropylmethoxy-5-methoxy-2-pyridinecarboxylic acid (compound 2) with 3,5-dichloroaminopyridine N-oxide (compound 3) or N-Boc-dichloropyridoxide (compound 3a), according to the scheme below:

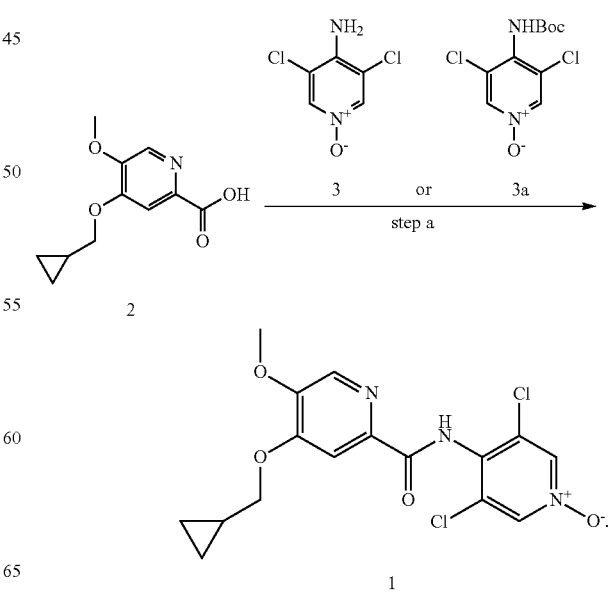

9. A compound of formula 4 below:
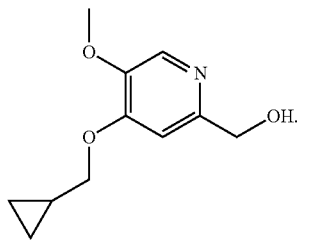
10. A compound of formula 6 below:
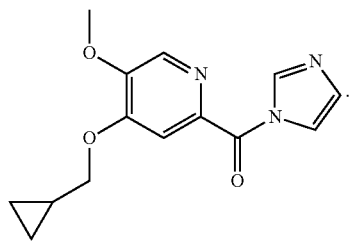 [SMILES: COc1cnc(C(=O)n2ccnc2)cc1OCC1CC1]
* * * * *